United States Patent
Ghanbari et al.

(10) Patent No.: US 10,166,303 B2
(45) Date of Patent: Jan. 1, 2019

(54) RADIO-IMAGING AND RADIO-THERAPY OF CANCER USING ANTIBODIES TO HAAH

(71) Applicant: Panacea Pharmaceuticals Inc., Gaithersburg, MD (US)

(72) Inventors: Hossein A. Ghanbari, Potomac, MD (US); Steven Andrew Fuller, Silver Spring, MD (US)

(73) Assignee: Panacea Pharmaceutical Inc., Gaithersburg, MD (US)

( * ) Notice: Subject to any disclaimer, the term of this patent is extended or adjusted under 35 U.S.C. 154(b) by 141 days.

(21) Appl. No.: 15/174,239

(22) Filed: Jun. 6, 2016

(65) Prior Publication Data

US 2016/0354499 A1    Dec. 8, 2016

Related U.S. Application Data

(60) Provisional application No. 62/171,454, filed on Jun. 5, 2015.

(51) Int. Cl.
| | |
|---|---|
| *A61K 51/00* | (2006.01) |
| *A61M 36/14* | (2006.01) |
| *A61K 51/10* | (2006.01) |
| *C07K 16/40* | (2006.01) |
| *C07K 16/30* | (2006.01) |
| *A61K 39/395* | (2006.01) |
| *A61K 39/00* | (2006.01) |

(52) U.S. Cl.
CPC ........ *A61K 51/1045* (2013.01); *A61K 39/395* (2013.01); *A61K 51/1075* (2013.01); *A61K 51/1093* (2013.01); *A61K 51/1096* (2013.01); *C07K 16/30* (2013.01); *C07K 16/40* (2013.01); *A61K 2039/505* (2013.01); *C07K 2317/21* (2013.01); *C07K 2317/73* (2013.01)

(58) Field of Classification Search
CPC ................ A61K 51/00; A61K 51/1045; A61K 51/1096; A61K 51/1093; A61K 51/1075; C07K 16/40; C07K 16/30; C07K 2317/73; C07K 2317/21
USPC .......... 424/1.11, 1.49, 1.65, 1.69, 1.81, 1.85, 424/1.89, 9.1, 9.2, 9.3, 9.4, 9.5, 9.6; 514/1, 1.1
See application file for complete search history.

(56) References Cited

U.S. PATENT DOCUMENTS

| | | | |
|---|---|---|---|
| 7,413,737 B2 * | 8/2008 | Wittrup | C07K 16/40 424/142.1 |
| 2014/0356930 A1 * | 12/2014 | Ghanbari | A61K 47/6807 435/236 |
| 2018/0036424 A1 * | 2/2018 | Ghanbari | A61K 47/6807 |

* cited by examiner

*Primary Examiner* — D. L. Jones
(74) *Attorney, Agent, or Firm* — John W. Ryan

(57) ABSTRACT

The present invention is directed to compositions and method for providing radio-imaging and radiotherapy for cancer. In particular, methods for making and using radio-labeled anti-HAAH antibodies for tumor imaging and immunotherapy are provided.

12 Claims, 5 Drawing Sheets

RADIO-IMAGING AND RADIO-THERAPY OF CANCER USING ANTIBODIES TO HAAH

BACKGROUND OF THE INVENTION

Substantial efforts have been directed to developing tools useful for early diagnosis and treatment of the various forms of cancer. Nonetheless, a definitive diagnosis is often dependent on exploratory surgery which is inevitably performed after the disease has advanced past the point when early treatment may be effected. Further, many treatment methods are general and fail to specifically target cancer cells. One promising method for early diagnosis and treatment of various forms of cancer is the identification of specific biochemical moieties, termed antigens, present on the surface of cancerous cells. Antibodies which will specifically recognize and bind to the antigens present on the surfaces of cancer cells potentially provide powerful tools for the diagnosis and treatment of the particular malignancy. Tumor specific cell surface antigens have previously been identified for certain melanomas, lymphomas, malignancies of the colon and reproductive tract. Thus, cell surface markers and antibodies which specifically recognize such a cell surface marker are valuable in the early detection and treatment of cancers.

Tumor specific antigens may also be useful in tumor imaging techniques. Imaging techniques have become an important element of early detection for many cancers. But imaging is not simply used for detection. Imaging is also important for determining the stage (telling how advanced the cancer is) and the precise locations of cancer to aid in directing surgery and other cancer treatments, or to check if a cancer has returned.

Tumor specific antigens may also be useful in methods of radio-immunotherapy. The treatment of cancer by radio-immunotherapy involves injecting the patient with a radioactive isotope connected to a specific cancer cell vector such as a monoclonal antibody (i.e., a radioimmunoconjugate), with the aim of selectively destroying targeted tumor cells. During radioactive decay, photons, electrons or even heavier particles are emitted and damage or kill cells along their trajectory.

Human aspartyl (asparaginyl) β-hydroxylase (HAAH), also known as aspartate β-hydroxylase (ASPH) is normally localized to the endoplasmic reticulum, however upon cellular transformation it is translocated to the cell surface. Over-expression of the enzyme HAAH has been detected in many cancers tested including lung, liver, colon, pancreas, prostate, ovary, bile duct, and breast. HAAH is highly specific for cancer and is not significantly present in adjacent non-affected tissue, or in tissue samples from normal individuals. HAAH functions to hydroxylate aspartyl or asparaginyl residues within EGF-like domains of specific proteins. While the natural substrates of HAAH remain unknown, potential target proteins containing EGF-like domains include those involved in cellular signaling (e.g., notch) and/or cell/extra-cellular matrix interactions (e.g., tenascin).

SUMMARY OF THE INVENTION

The present invention encompasses compositions and methods for tumor imaging and immunotherapy comprising radiolabeled antibodies targeting Aspartyl-(Asparaginyl)-β-hydroxylase (HAAH)

The invention further encompasses compositions and methods for detecting, diagnosing, and/or evaluating cancer in a mammal by contacting a tissue or bodily fluid from the mammal with a radiolabeled antibody which binds to a HAAH polypeptide under conditions sufficient to form an antigen-antibody complex.

Antibodies of the invention include, but are not limited to, monoclonal antibodies, synthetic antibodies, recombinantly produced antibodies, intrabodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab')$_2$ fragments, disulfide-linked Fvs (sdFv), and epitope-binding fragments of any of the above.

The antibodies used in the methods of the invention may be derived from any animal origin including birds and mammals (e.g., human, murine, donkey, sheep, rabbit, goat, guinea pig, camel, horse, or chicken).

The antibodies used in the methods of the present invention may be monospecific, bispecific, trispecific or of greater multispecificity. Multispecific antibodies may immunospecifically bind to different epitopes of an HAAH polypeptide or may immunospecifically bind to both an HAAH polypeptide as well a heterologous epitope, such as a heterologous polypeptide or solid support material.

The present invention contemplates radioimmunoconjugates comprising a chelating agent, a radioisotope, and a fully human anti-HAAH antibody.

The present invention encompasses radioimmunoconjugates comprising an alpha-emitting radioisotope bound to a fully human anti-HAAH antibody.

The present invention also encompasses radioimmunoconjugates comprising a beta-emitting radioisotope bound to a fully human anti-HAAH antibody.

The present invention also encompasses radioimmunoconjugates comprising a gamma-emitting radioisotope bound to a fully human anti-HAAH antibody.

The present invention further encompasses radioimmunoconjugates comprising $^{213}$Bi, $^{90}$Y or $^{111}$In bound to a fully human anti-HAAH antibody.

One embodiment of the present invention encompasses methods for killing cancer cells, comprising the steps of conjugating a radioactive isotope to an antibody which binds to human aspartyl (asparaginyl) β-hydroxylase (HAAH) and contacting cancer cells with the radiolabeled antibody which binds to HAAH.

One embodiment of the present invention encompasses methods for killing cancer cells in a mammal, comprising the steps of conjugating a radioactive isotope to an antibody which binds to human aspartyl (asparaginyl) β-hydroxylase (HAAH) and contacting cancer cells with the radiolabeled antibody which binds to HAAH.

Another embodiment of the present invention encompasses method for treating cancerous tissue in a mammal, comprising the steps of conjugating a radioisotope to an antibody which binds to human aspartyl (asparaginyl) β-hydroxylase (HAAH) and contacting cancerous tissue of said mammal with the radiolabeled antibody which binds to HAAH.

A further embodiment of the present invention contemplates a method for radio-imaging a tumor in a mammal, comprising contacting a tissue of said mammal with a radiolabeled antibody which binds to HAAH and then visualizing the resulting tissue-antibody-radiolabel using imaging instruments and associated software, such as single-photon emission computed tomography (SPECT) or positron emission tomography (PET).

DETAILED DESCRIPTION OF THE INVENTION

Figure 1:
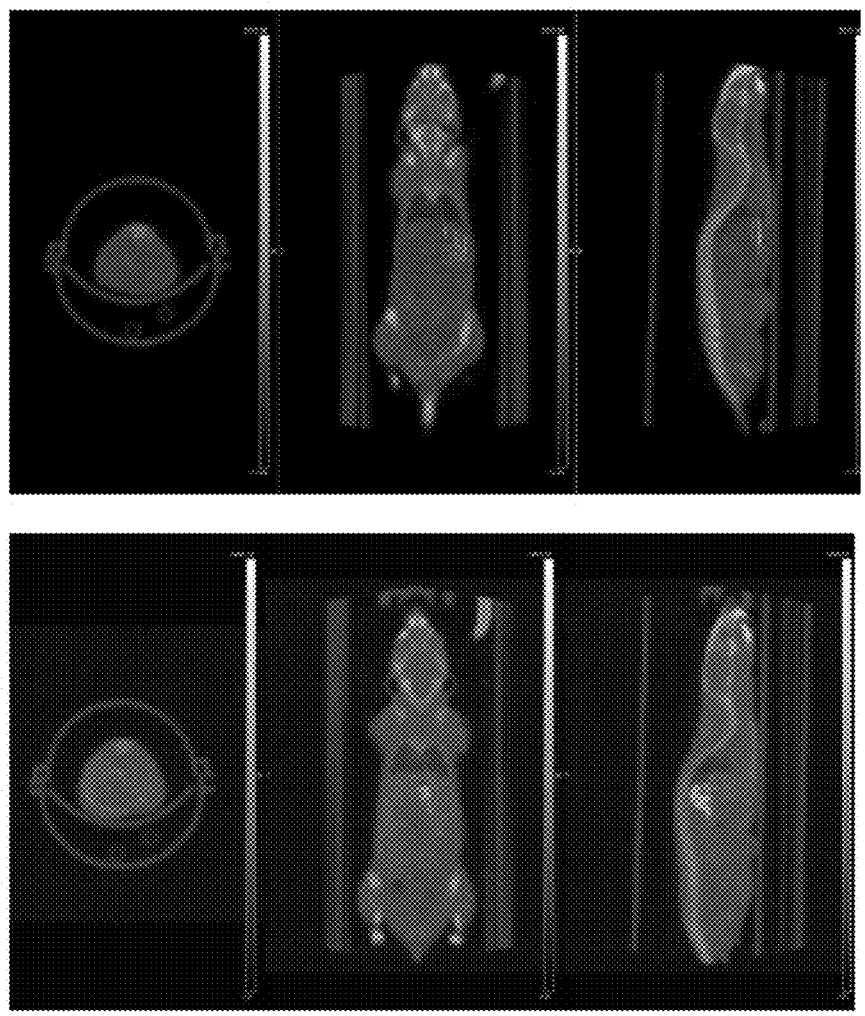
FIG. 1 shows a SPECT/CT of 4T1 tumor bearing mice at 4 hrs (upper panel treated, lower untreated).

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implemented in other systems, and that any such variation would be within such modifications that do not part from the scope of the present invention. Before explaining the disclosed embodiments of the present invention in detail, it is to be understood that the invention is not limited in its application to the details of any particular arrangement shown, since the invention is capable of other embodiments. The terminology used herein is for the purpose of description and not of limitation. Further, although certain methods are described with reference to certain steps that are presented herein in certain order, in many instances, these steps may be performed in any order as would be appreciated by one skilled in the art, and the methods are not limited to the particular arrangement of steps disclosed herein.

The cancer tumor marker, human aspartyl (asparaginyl) β-hydroxylase (HAAH), also known as aspartate β-hydroxylase (ASPH) is found on the cell surface of cancer cells, but not on the surface of normal cells. As such, HAAH provides a cancer-specific target for anti-HAAH antibodies for tumor imaging and immunotherapy. Antibodies to HAAH are described in U.S. Pat. No. 7,413,737 and are commercially available from Panacea Pharmaceuticals, Inc. In particular, Panacea Pharmaceuticals, Inc. has developed PAN-622, a fully human anti-HAAH antibody. Antibodies to HAAH are internalized upon binding to the target cell. Antibodies may be radiolabeled by direct chemical conjugation (for example, with $^{124}$iodine or $^{131}$iodine) or may be conjugated to chelating agents that will bind to many different radioisotopes (for example, $^{111}$ indium or $^{64}$copper). The radiolabeled antibodies are then injected into the bloodstream of a patient, will bind specifically to the tumor cells, if present, and the resulting tissue-antibody-radiolabel complex can be visualized using imaging instruments and associated software, such as single-photon emission computed tomography (SPECT) or positron emission tomography (PET).

In the therapeutic usage, the radiolabeled antibodies are injected into the bloodstream of a patient, will bind specifically to the tumor cells, if present, and the cells will be killed by the radiation emission (using for example, $^{90}$ yttrium, a strong beta emitter).

The choice of the particular radioisotope with which the antibody is labeled may be determined by the size of the tumor to be treated and its localization in the body. Emission range in the tissue and half-life are important characteristics to consider when choosing a radioisotope.

Alpha emitters, which have a short emission range in comparison to beta emitters, may be preferable for treatment of small tumors or melanomas that are disseminated in the body. Examples of alpha emitters include $^{211}$At, $^{212}$Bi, $^{213}$Bi, $^{223}$Ra, $^{224}$Ra, $^{225}$AC, $^{212}$Pb, and $^{227}$Th.

Beta emitters have a longer emission range and may be preferable for the treatment of large tumors or melanomas. Examples of beta emitters include $^{188}$Re, $^{90}$Y, $^{32}$, $^{47}$Sc, $^{67}$Cu, $^{64}$Cu, $^{77}$As, $^{89}$Sr, $^{105}$Rh, $^{109}$Pd, $^{111}$Ag, $^{131}$I, $^{177}$Lu, $^{153}$Sm, $^{159}$Gd, $^{186}$Re, $^{166}$Ho, $^{166}$Dy, $^{140}$La, $^{194}$Ir, $^{198}$Au, and $^{199}$Au.

Gamma emitters include $^{67}$Ga, $^{111}$In, $^{134}$Ce, and $^{129}$I.

Positron emitters could also be used and include $^{52m}$Mn, $^{62}$Cu, $^{68}$Ga, $^{11}$C, $^{82}$Rn $^{110}$In, $^{118}$Sb, $^{122}$I, $^{18}$F, $^{38}$K, $^{51}$Mn, $^{52}$Mn, $^{52}$Fe, $^{55}$Co, $^{61}$Cu, $^{64}$Cu, $^{72}$As, $^{75}$Br, $^{76}$Br, $^{83}$Sr, $^{86}$Y, $^{89}$Zr, $^{120}$I, and $^{124}$I.

Any of the radioisotopes, except alpha emitters, that are used for radioimmunotherapy may also be used at lower doses for radioimmunoimaging, for example a beta emitter, a positron emitter or an admixture of a beta emitter and a positron emitter.

U.S. Pat. No. 5,641,471, herein incorporated in its entirety by reference, discloses a method for preparing $^{213}$Bi for therapeutic use, wherein a monoclonal antibody is used as targeting moiety. A chelator such as CHX-DTPA (cyclohexyldiethylenetriamine pentaacetic acid) may be attached to the antibody and functions to chelate the radioisotope. The radioisotope may then be delivered to the target cell where it can kill it.

Example 1

As a specific example, the fully human monoclonal anti-HAAH antibody, PAN-622 is conjugated to a chelating agent such as (R)-1-Amino-3(4-isothiocyanatophenyl)propyl]-trans-(S,S)-cyclohexane-1,2-diamine-pentaacetic acid (CHX-A"-DTPA) or 1,4,7,10-tetranzacyclododecane-1,4,7,10-tetraacetic acid (DOTA). For tumor imaging purposes, a gamma emitter, such as indium-111 is mixed with PAN-622 chelate conjugate, the mixture injected into a patient and the tumor cells imaged with SPECT. As an alternative, PAN-622 is conjugated to a chelating agent such as 1,4,8,11-tetraazacyclotetradecane-1,4,8, 11-tetraacetic acid (TETA). For tumor imaging purposes, a positron emitter, such as copper-64 is mixed with PAN-622 chelate conjugate, the mixture injected into a patient and the tumor cells imaged with PET.

Example 2

For radioimmunotherapy, the fully human monoclonal anti-HAAH antibody, PAN-622 is conjugated to a chelating agent such as (R)-1-Amino-3(4-isothiocyanatophenyl)propyl]-trans-(S,S)-cyclohexane-1,2-diamine-pentaacetic acid (CHX-A"-DTPA) or 1,4,7,10-tetraazacyclododecane-1,4,7,10-tetrancetic acid (DOTA). For therapeutic purposes, a strong beta emitter, such as yttrium-90 is mixed with PAN-622 chelate conjugate and the mixture injected into a patient to kill the tumor cells.

Example 3

Killing of K562 and CCRF-CEM Leukemia Cells with High Specific Activity $^{213}$Bi-PAN-622 Antibody The cells arrived in 50 mL media in Falcon tubes. The concentration of CCRF-CEM was 4×10$^5$ cells/mL (13 mL total); of K562-1.0×10$^6$ cells/mL (45 mL total). The cells were spun down at 2,000 rpm for 10 min and taken up in 2.6 and 22.5 mL PBS, respectively, to reach the cellular concentration of 2×10$^6$ cells/mL. 0.5 mL of each cell suspension were transferred into the 1.5 mL metal-free low protein binding Eppendorf tubes, containing 0.5 mL of PBS, so the final cell concentration became $10^6$ cells/mL. For K562 both specific killing with $^{213}$Bi-DTPA-PAN-622 and non-specific with $^{213}$Bi-2556 isotype-matching mAbs was performed, for CCRF-CEM cells only specific killing was investigated because of the small number of cells available.

10 μg (2.3 μL) of DTPA-PAN-622 mAb was radiolabeled with 1 mCi $^{213}$BiI$_3$ in 200 μL of ammonium acetate solution with the final specific activity of 100 mCi/mg. The reaction mixture was diluted to 1000 μL, so that the $^{213}$Bi-DTPA-PAN-622 concentration became 0.01 mg/mL=66 nM. 0.1 μL (0.1 μCi), 1 μL (1 μCi) and 10 μL (10 μCi) of the $^{213}$Bi-DTPA-PAN-622 were added to the cells suspensions in duplicate for K562 cells and in singlicate to CCRF-CEM cells. The same concentrations of the control radiolabeled DTPA-2556 mAb to HIV-1 gp41 were added to the control samples of K562 suspensions. The cells were incubated with the radiolabeled mAbs for 1 hr at 37° C. at gentle agitation of 100 rpm, spun down, the supernatants with the unbound radiolabeled mAbs were discarded and the cells were taken up in their respective media, plated in 96 well plates in 9 wells for each sample (triplicate for each time point) and placed into the CO$_2$ incubator at 37° C. for 72 hrs. At 24, 48 and 72 hrs recovery period the dead cells were innumerated with Trypan blue assay. The killing results are presented in Table 1 below.

Figure 2:
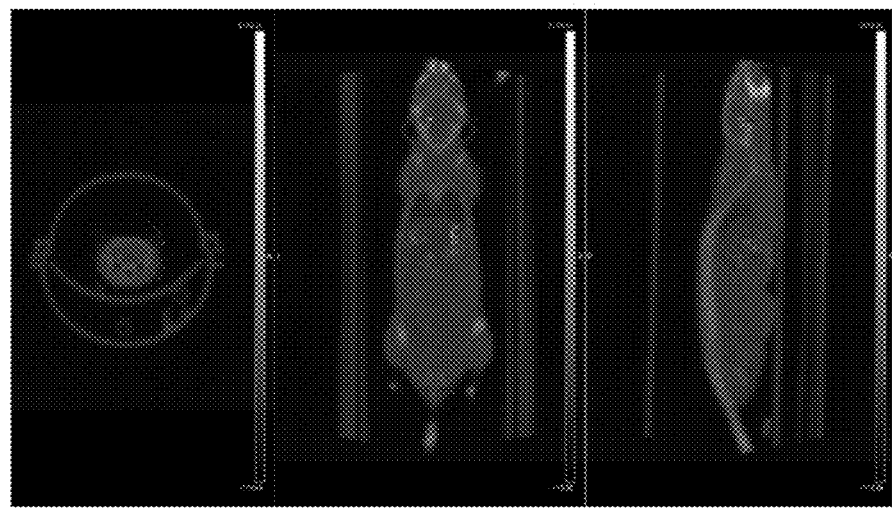
FIG. 2 shows a SPECT/CT of 4T1 tumor bearing mice at 24 hrs (upper panel treated, lower untreated).
Figure 2:
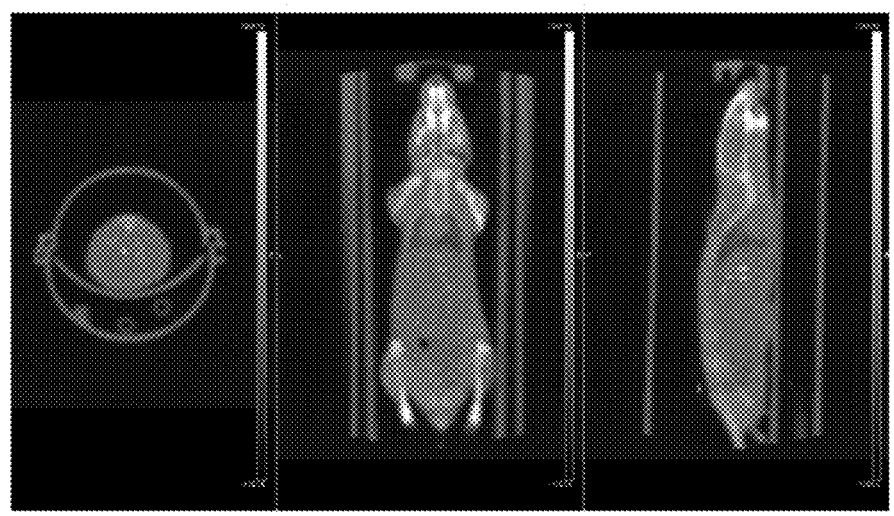
Figure 3:
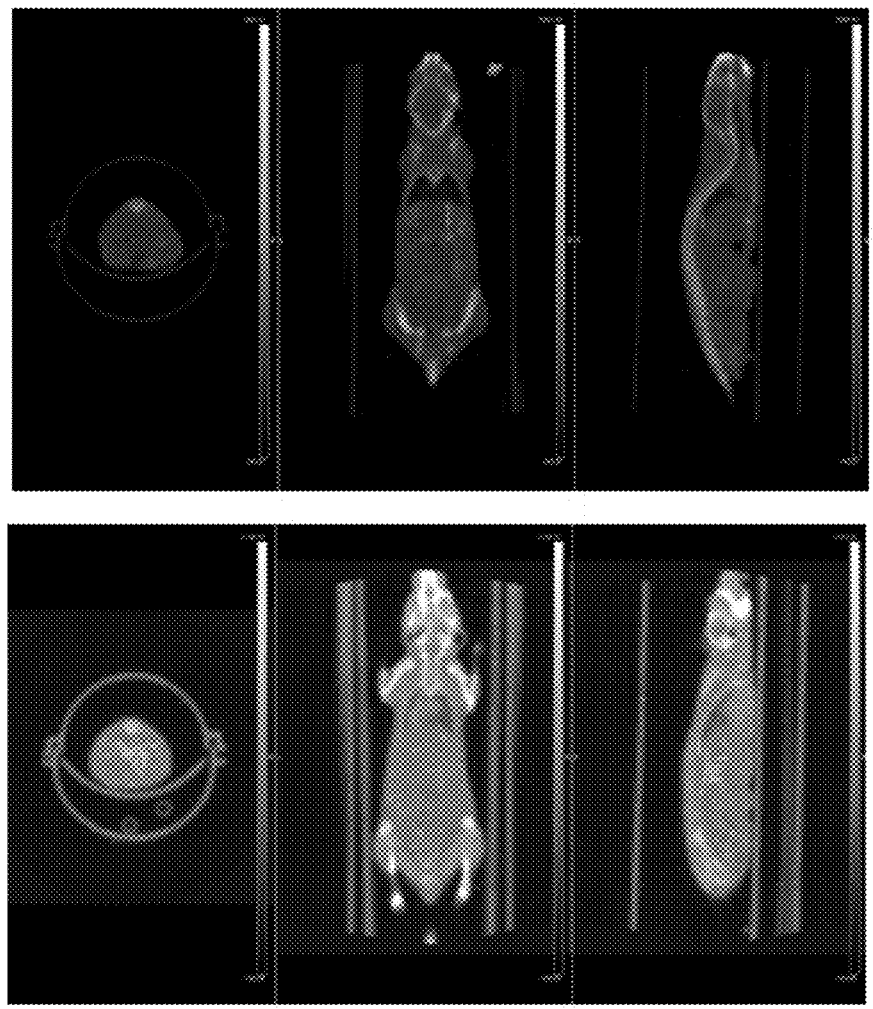
FIG. 3 shows a SPECT/CT of 4T1 tumor bearing mice at 48 hrs (upper panel treated, lower untreated).
Figure 4:
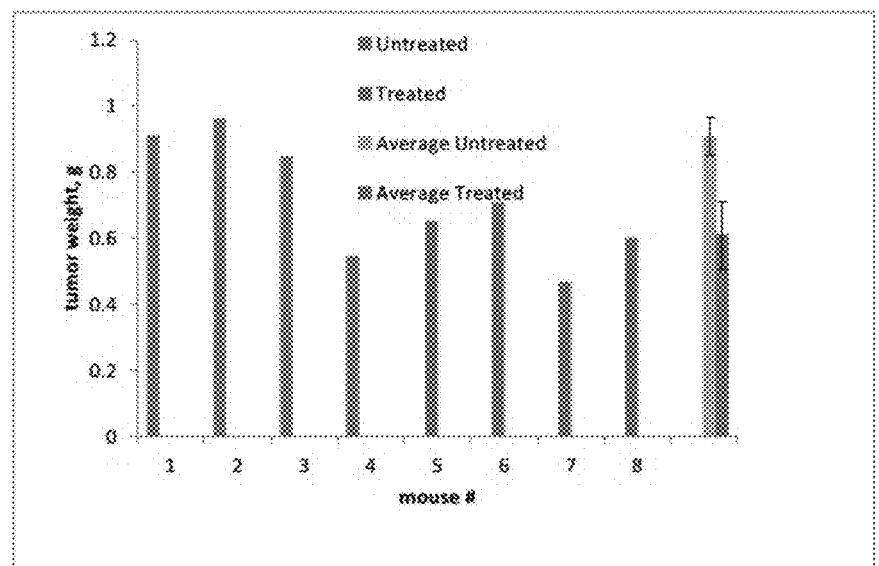
FIG. 4 shows the weights of the primary tumors from 4T1 tumor-bearing mice.
Figure 5:
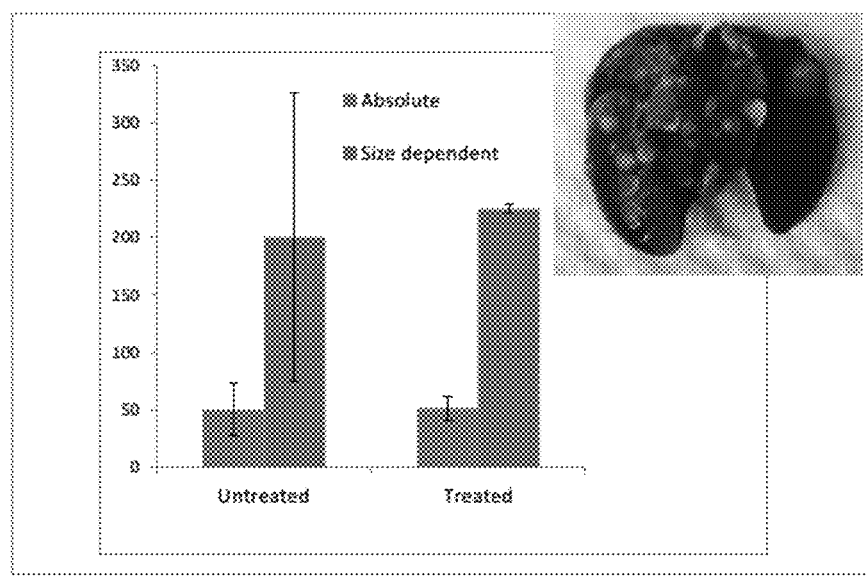
FIG. 5 shows the the number of the metastases in the lungs of 4T1-tumor bearing mice and the photograph of the India ink-perfused lungs from the untreated mouse (insert).

At all time points there was significant uptake of in the peritoneum of the untreated mice which was practically absent in the $^{213}$Bi-PAN-622-treated mice (FIG. 1-3). This can be explained by the micrometastatic spread of the tumor cells in the peritoneum. In treated mice the majority of activity was concentrated in the liver where the antibody is metabolized. There was some uptake in the heads of all mice which should be investigated in regard to HAAH expression in head and neck. There was some diffuse uptake of $^{111}$In-PAN-622 in the lungs of the untreated mice, and no visible uptake in the lungs of $^{213}$Bi-PAN-622-treated mice. The pathological investigation revealed that the weight of the primary tumors was significantly (P=0.4) less in $^{213}$Bi-PAN-622-treated mice than in untreated (FIG. 4). The number of metastases in the lungs of both groups was practically the same (FIG. 5), however, it might be possible that some of those metastases in the $^{213}$Bi-PAN-622-treated group do not have any cells left expressing HAAH and for that reason there is no uptake on the microSPECT/CT images. Also, one week between the last imaging session and opening of the mice might have contributed to the emergence of the additional lung metastases.

While the invention has been described with reference to certain exemplary embodiments thereof, those skilled in the art may make various modifications to the described embodiments of the invention without departing from the

TABLE 1

| Concentration and dose of $^{213}$Bi-pan622 | Cells dead by Trypan blue assay in a total cell population, % | | | | | | | | | | | |
|---|---|---|---|---|---|---|---|---|---|---|---|---|
| | 0 | | | 0.006 nM (0.1 μCi) | | | 0.06 nM (1 μCi) | | | 0.6 nM (10 μCi) | | |
| Time, hrs | 24 | 48 | 72 | 24 | 48 | 72 | 24 | 48 | 72 | 24 | 48 | 72 |
| K562 | 6 ± 1 | 11 ± 2 | 10 ± 1 | 6 ± 1 | 10 ± 2 | 11 ± 0.5 | 5 ± 2 | 12 ± 2 | 15 ± 2 | 7.6 ± 1 | 14 ± 2 | 24 ± 4 |
| CCRF-CEM | 38 ± 4 | 52 ± 5 | 50 ± 3 | 36 ± 5 | 60 ± 5 | 86 ± 4 | 53 ± 6 | 79 ± 7 | 89 ± 7 | 77 ± 6 | 88 ± 4 | 99 ± 4 |

No killing of K562 cells with the same activities of $^{213}$Bi-2556 isotype-matching control mAb was detected.

The killing of leukemic cells in vitro with $^{213}$Bi-DTPA-PAN-622 was time dependent with no killing seen at 24 hrs for the lowest activity for both cell lines and the maximal killing observed at 72 hrs post treatment for both cells lines. Total killing for all doses of $^{213}$Bi-DTPA-PAN-622 was higher than in the previous experiment when $^{213}$Bi-DTPA-PAN-622 with the specific activity of 10 mCi/mg was used.

Example 4

4T1 Tumor Treatment with $^{213}$Bi-Pan622 and SPECT/CT Imaging Study with $^{111}$In-Pan622 Antibody in a Mouse Model Eight 6-8 weeks old female BALB/c mice were injected intradermally into the mammary fat pad with $10^5$ 4T1 cells. The primary tumors in mammary fat pad became palpable in all mice on Day 10 post cell injection. In this model the lung metastases start to appear approximately on Day 14 post cell injection. Four mice were treated on Days 5 and 8 post-cell injection with 150 μCi $^{213}$Bi-PAN-622 each time via IP injection while the other four were left untreated. On Day 21 post-cell injection all tumor-bearing mice were given IP 200 μCi $^{111}$In-PAN-622 and imaged at 4, 24 and 48 hrs after administration of $^{111}$In-PAN-622 with microSPECT/CT. One week after the last imaging time point the mice were sacrificed, their primary tumors removed and weighted and their lungs were perfused with India ink and the metastases quantified.

scope of the invention. The terms and descriptions used herein are set forth by way of illustration only and not meant as limitations. In particular, although the present invention has been described by way of examples, a variety of compositions and processes would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A method for killing cancer cells, comprising the steps of:
   conjugating a radioisotope to a PAN-622 antibody, an antibody which binds to human aspartyl (asparaginyl) ß-hydroxylase (HAAH), to form a radiolabeled PAN-622 antibody and
   contacting cancer cells with the radiolabeled PAN-622 antibody in an amount sufficient to kill the cancer cells, wherein the radiolabeled PAN-622 antibody binds to HAAH, thereby killing the cancer cells.

2. The method of claim 1, wherein said radioisotope is selected from the group consisting of $^{213}$Bi, $^{90}$Y and $^{111}$In.

3. The method of claim 1, wherein the cancer cells are leukemia cells.

4. The method of claim 3, wherein the radioisotope is $^{213}$Bi.

5. A method for treating cancerous tissue in a mammal, comprising the steps of:

conjugating a radioisotope to a PAN-622 antibody, an antibody which binds to human aspartyl (asparaginyl) ß-hydroxylase (HAAH), to form a radiolabeled antibody and contacting cancerous tissue of said mammal with the radiolabeled antibody which binds to HAAH.

6. The method of claim 5, wherein said radioisotope is $^{213}$Bi.

7. The method of claim 5, wherein said radioisotope is $^{111}$In.

8. The method of claim 5, wherein said radioisotope is $^{90}$Y.

9. A radioimmunoconjugate comprising a chelating agent, a radioisotope, and a fully human anti-HAAH PAN-622 antibody.

10. The radioimmunoconjugate of claim 9, wherein the radioisotope is $^{213}$Bi.

11. The radioimmunoconjugate of claim 9, wherein the radioisotope is $^{111}$In.

12. The radioimmunoconjugate of claim 9, wherein said radioisotope is $^{90}$Y.

\* \* \* \* \*